United States Patent
Schmieding et al.

(10) Patent No.: US 8,328,716 B2
(45) Date of Patent: Dec. 11, 2012

(54) RETRACTING CANNULA

(75) Inventors: Reinhold Schmieding, Naples, FL (US); Randall L. Hacker, Naples, FL (US)

(73) Assignee: Arthrex, Inc., Naples, FL (US)

( * ) Notice: Subject to any disclaimer, the term of this patent is extended or adjusted under 35 U.S.C. 154(b) by 2301 days.

(21) Appl. No.: 10/443,893

(22) Filed: May 23, 2003

(65) Prior Publication Data
US 2004/0039400 A1    Feb. 26, 2004

Related U.S. Application Data

(60) Provisional application No. 60/382,343, filed on May 23, 2002.

(51) Int. Cl.
*A61B 1/32* (2006.01)

(52) U.S. Cl. ......... 600/184; 606/108; 606/191; 600/201

(58) Field of Classification Search .................. 606/190, 606/192, 198, 213, 184, 185, 191; 600/226, 600/201–219, 235, 184; 604/106–113, 264
See application file for complete search history.

(56) References Cited

U.S. PATENT DOCUMENTS

| | | | |
|---|---|---|---|
| 4,506,673 A * | 3/1985 | Bonnell | 607/50 |
| 5,226,890 A * | 7/1993 | Ianniruberto et al. | 604/164.04 |
| 5,290,249 A | 3/1994 | Foster et al. | |
| 5,320,610 A * | 6/1994 | Yoon | 604/158 |
| 5,342,384 A * | 8/1994 | Sugarbaker | 606/191 |
| 5,423,770 A * | 6/1995 | Yoon | 604/506 |
| 5,716,325 A | 2/1998 | Bonutti | |
| 5,895,351 A * | 4/1999 | Nottage et al. | 600/201 |
| 5,919,196 A * | 7/1999 | Bobic et al. | 606/86 |
| 6,520,907 B1 * | 2/2003 | Foley et al. | 600/114 |
| 6,695,839 B2 * | 2/2004 | Sharkey et al. | 606/49 |

* cited by examiner

*Primary Examiner* — Kathleen Sonnett
(74) *Attorney, Agent, or Firm* — Dickstein Shapiro LLP

(57) ABSTRACT

A retracting two-piece cannula for distracting soft tissue from bone (e.g., the articular surface of a knee) to provide a surgical workspace for osteochondral repair. After inserting an outer cannula provided with a threaded outer surface into an incision (preferably widened by one or more dilators), the outer cannula is rotated to engage the threaded outer surface with the soft tissue to be distracted. An inner cannula is then inserted into the outer cannula and advanced until it contacts the articular surface. Further relative movement between the inner and outer cannulas causes the outer cannula to be drawn away from the articular surface, thereby retracting the soft tissue and establishing the workspace. The inner and outer cannula are then locked together to maintain the workspace, and an osteochondral core may be introduced through the inner cannula.

8 Claims, 4 Drawing Sheets

RETRACTING CANNULA

This application claims the benefit of U.S. Provisional Application Ser. No. 60/382,343, filed May 23, 2002, the disclosure of which is hereby incorporated by reference.

BACKGROUND OF THE INVENTION

Many reconstructive orthopedic surgeries can be performed either as open procedures or as arthroscopic procedures. Rapid recovery from arthroscopic surgical procedures makes them generally more preferred over open surgical procedures. Arthroscopic procedures, however, are difficult to perform in small workspaces, such as within a joint. Typically, an arthroscopic workspace is maintained by the ingress of pressurized fluid into the involved joint to separate the soft tissue from the joint surface. The size of the workspace that can be maintained solely by fluid pressure is restricted by practical limitations, however.

U.S. Pat. No. 5,919,196 issued Jul. 6, 1999 to Bobic et al. discloses a method and apparatus for repair of articular cartilage, such as in the knee, using osteochondral cores. The procedure can be performed arthroscopically, but as a practical matter open procedures must be used when articular cores larger than about 10 mm in diameter are indicated, due to the practical limitations of maintaining an arthroscopic workspace of sufficient size to accommodate the larger cores and associated harvesting instruments.

SUMMARY OF THE INVENTION

The present invention overcomes the limitations of the prior art by providing a retracting cannula. The retracting cannula is used for distracting tissue to provide a surgical workspace. The retracting cannula of the present invention is especially useful for maintaining a workspace in the knee joint for arthroscopic osteochondral transplantation procedures.

The retracting cannula of the present invention preferably comprises an outer cannula with a threaded outer surface for engaging the soft tissue to be distracted and an inner cannula with a curved distal end for contacting and sealing the bone surface of a joint, such as the articular surface of a knee. The outer cannula is slidably disposed over the inner cannula. After the inner cannula contacts the articular surface, further relative movement between the inner cannula and the outer cannula causes the soft tissue to distract from the articular surface. The outer cannula can be engaged with the inner cannula to maintain the soft tissue in a distracted position with respect to the articular surface. In a preferred embodiment of the invention, the engagement between the inner and outer cannulas is accomplished with a post on the inner cannula which is rotatably engaged in a J-hook slot in the outer cannula. The retracting cannula is preferably formed of a polymer, preferably a clear polymer such as polycarbonate.

In the method of using the present invention, at least one dilator is first inserted into an incision made through the soft tissue. A second dilator is preferably inserted over the first dilator to widen the portal. The outer cannula is then advanced over the dilators and threaded into the soft tissue. The dilators are then removed, and the inner cannula is inserted into the outer cannula and slidably advanced relative to the outer cannula such that the distal end of the inner cannula contacts and seals the surface of the joint. Further advancement of the inner cannula relative to the outer cannula causes the tissue engaged by the threaded surface of the outer cannula to be drawn away from the inner tissue to establish the workspace. The inner and outer cannulas are then locked together (by rotatably engaging the post on the inner cannula into the J-hook slot in the outer cannula) to maintain the arthroscopic workspace. Arthroscopic osteochondral transplantation surgery can then be performed through the inner cannula.

Other features and advantages of the present invention will become apparent when the following description is read in conjunction with the accompanying drawings.

DETAILED DESCRIPTION OF THE PREFERRED EMBODIMENT

Figure 1:
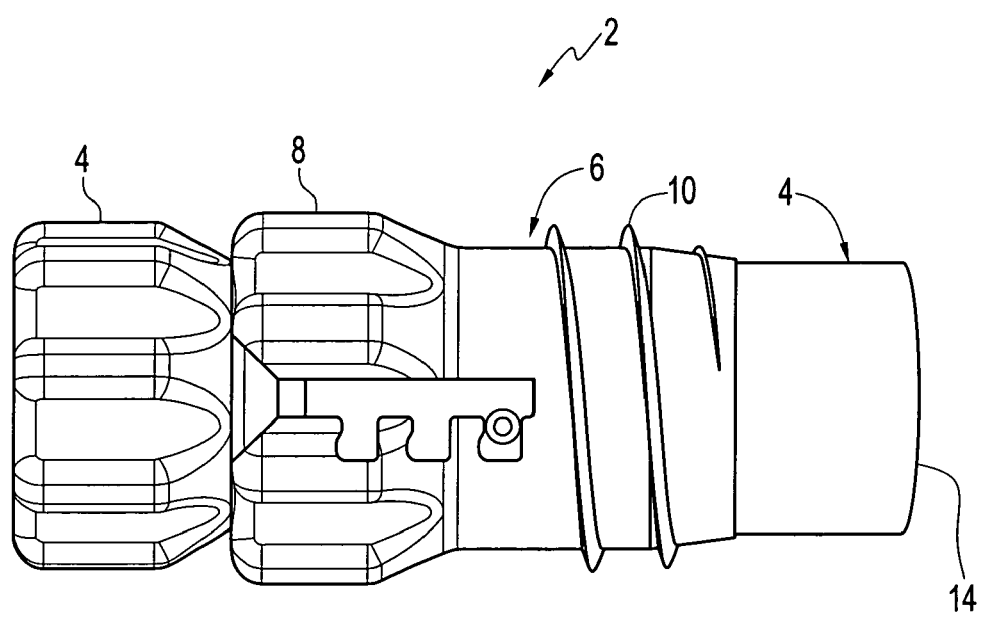
FIG. 1 is a perspective view of the retracting cannula of the present invention.

Referring first to FIG. 1, the retracting cannula of the present invention, identified generally by reference numeral 2, comprises two primary components: an inner cannula 4 and an outer cannula 6. Outer cannula 6 includes a finger grip 8 on its proximal end and has a slightly tapered distal end. Outer cannula 6 is provided with a threaded outer surface 10 for engaging soft tissue 12 to be distracted, as described in greater detail below.

Figure 7:
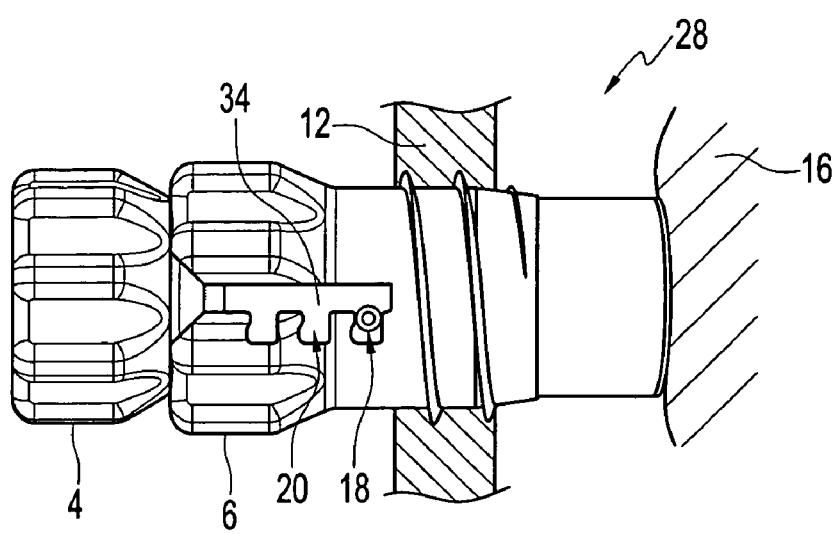
FIG. 7 is a side view of the inner and outer cannula with the inner cannula fully advanced against the joint surface, such that the outer cannula retracts the soft tissue with which it is engaged.

Inner cannula 4 has a curved distal end 14 for contacting and sealing the surface of tissue 16, such as the surface of a joint, adjacent the soft tissue 12 to be distracted (see FIG. 7). Inner cannula 4 has a smooth outer surface and is dimensioned such that outer cannula 6 can be slidably disposed over inner cannula 4. Inner cannula 4 is also engagable with outer cannula 6 by way of a post 18 on inner cannula 4 which can be rotated and engaged in one of a plurality of J-hook slots 20 provided in outer cannula 6, as described below with reference to FIG. 7.

In the preferred embodiment of the present invention, retracting cannula 2 is designed to create a workspace in the knee for osteochondral transplantation surgery, such that inner cannula 4 contacts the articular surface of the knee, and outer cannula 6 engages the surrounding soft tissue to be distracted. The cannula set is preferably provided in a range of sizes (e.g., with an inner cannula diameter ranging from 12 mm to 20 mm), and the appropriately sized set is selected such that the inner diameter of the inner cannula 4 is larger than the outer diameter of the osteochondral core to be installed. Once the workspace has been created and inner cannula 4 has been engaged with outer cannula 6, the osteochondral harvesting instruments and core are installed through inner cannula 4 The components of the present invention, including inner cannula 4 and outer cannula 6, are preferably are made of a clear polymer, such as polycarbonate (Lexan) and preferably are autoclavable.

Figure 2:
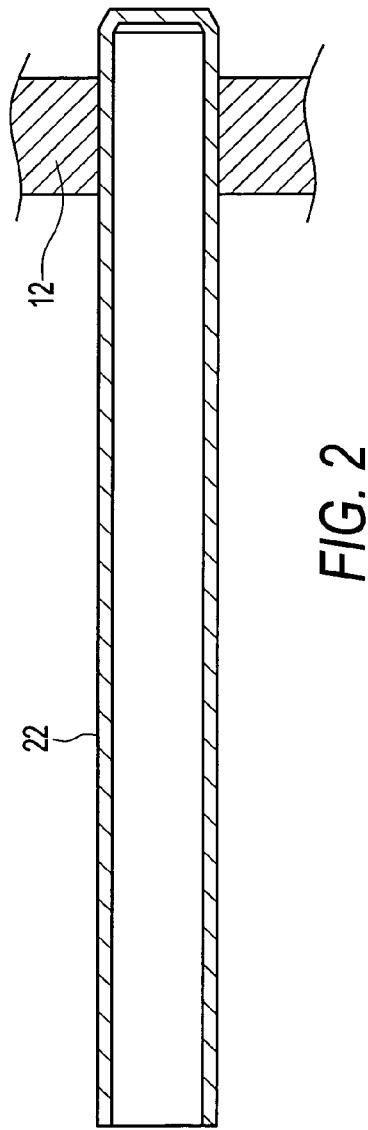
FIG. 2 is a cross-sectional view of a first dilator inserted into an incision in accordance with the method of the present invention.
Figure 3:
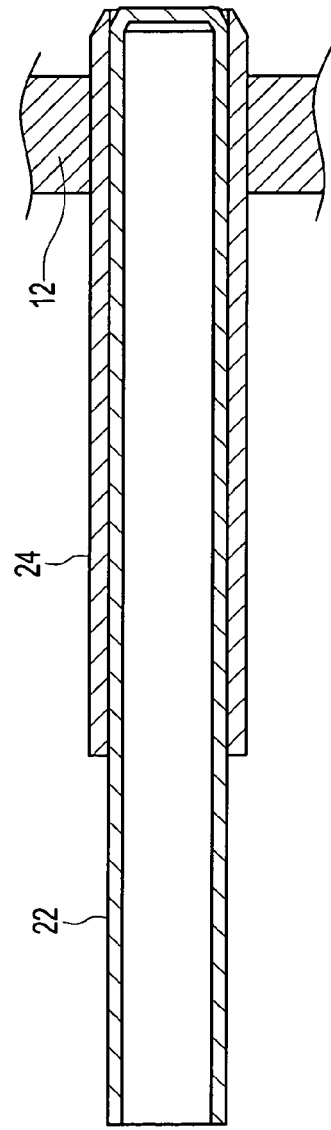
FIG. 3 is a cross-sectional view of a second dilator inserted over the first dilator in accordance with the method of the present invention.
Figure 4:
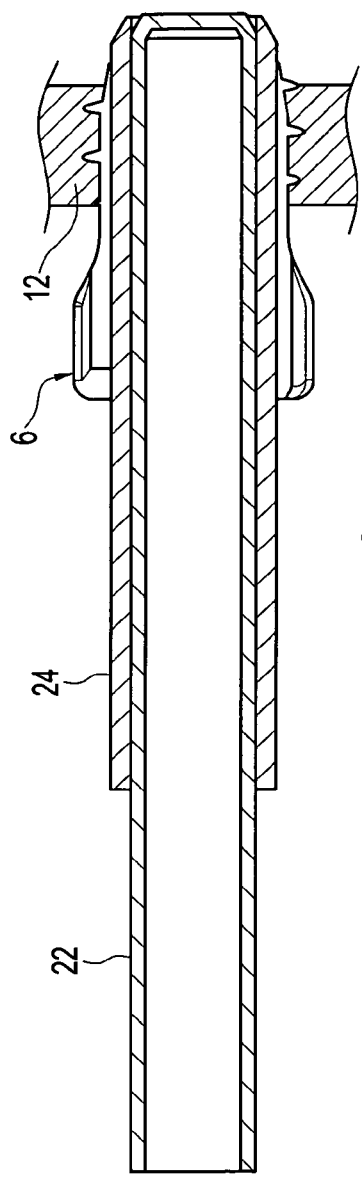
FIG. 4 and FIG. 5 are cross-sectional and side views, respectively, of the outer cannula of the present invention inserted over the first and second dilators.
Figure 5:
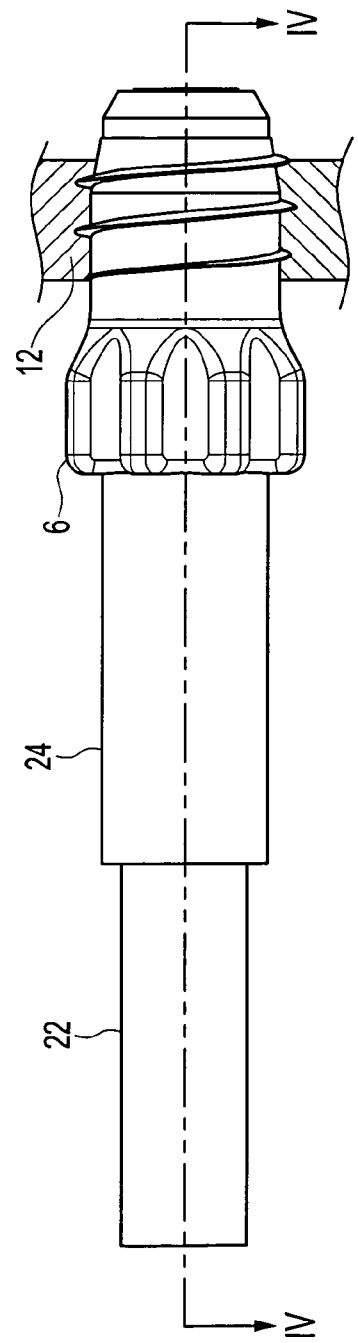
Figure 6:
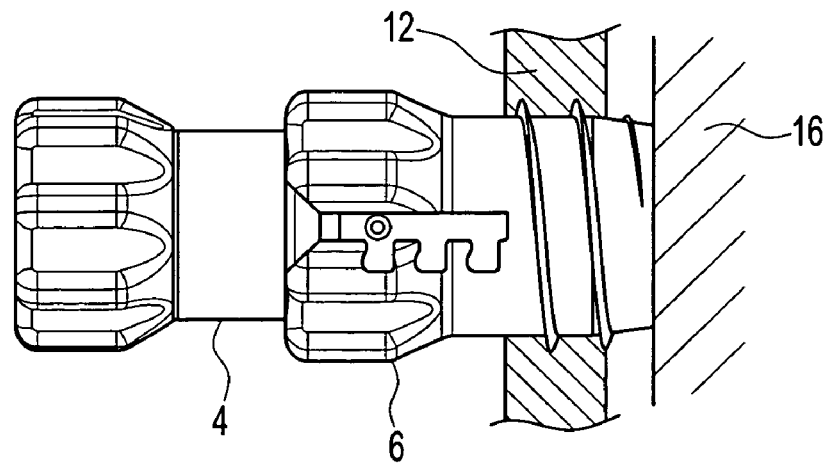
FIG. 6 is a side view of the inner cannula inserted into the outer cannula at an initial stage of insertion.

Referring to FIG. 2, in the method of the present invention, a first dilator 22 is inserted into an incision made in soft tissue 12. Prior to making the incision, a proper location is determined so that the first dilator 22 can be inserted at a straight angle with respect to the operative area. Preoperative diagnostics may include an arthroscopic assessment of the patient to get correct location, or other non-invasive procedures, such as MRI. Referring to FIG. 3, following insertion of dilator 22, a second dilator 24 is inserted (over the first dilator 22) to further expand the incision. Outer cannula 6 is then inserted over the second dilator 24 and rotated until the threads 10 on the outer surface of outer cannula 6 engage the soft tissue 12, as shown in the cross-sectional and side views of FIGS. 4 and 5. First dilator 22 and second dilator 24 are then removed, leaving outer cannula 4 engaged with outer tissue 12. Next, inner cannula 4 is slidably advanced into outer cannula 6 until the distal end of inner cannula 6 abuts against the surface of the joint 16, as shown in FIG. 6. As shown in FIG. 7, as inner cannula 4 is advanced, outer cannula 6 is drawn back relative to inner cannula 4, pulling soft tissue 12 away from joint surface 26 to establish a surgical workspace 28.

When sufficient separation has been achieved to create the desired surgical workspace 28, inner cannula 4 is rotated such that post 18 is turned into and engages one of a plurality of J-hook notches 30 on the outer cannula 6 to hold the outer cannula 6 in place relative to inner cannula 4. Other methods of locking the outer cannula in place relative to the inner cannula 4 could also be utilized. FIG. 7 depicts notch 20 on outer cannula 6 engaged with post 18 on inner cannula 4 to retain the soft tissue in its position relative to the joint surface. The relative position of the inner and outer cannulae can be adjusted by rotating the inner cannula 4 to align the post 18 with track 34, and reposition the post 18 in the appropriate J-hook slot in outer cannula 6. The notch nearest the threads provides the greatest amount of separation, as shown in FIG. 7.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A method for distracting soft tissue from a joint to provide a surgical workspace, comprising:
   inserting an outer cannula having a threaded outer surface into an incision made through the soft tissue;
   engaging the soft tissue with the threaded outer surface of the outer cannula;
   inserting an inner cannula into the outer cannula, the inner cannula having a distal end;
   slidably advancing the inner cannula relative to the outer cannula such that the distal end of the inner cannula contacts a surface of the joint; and
   moving the outer cannula relative to the inner cannula to cause the soft tissue engaged by the threaded surface of the outer cannula to be drawn away from the joint surface to establish the surgical workspace.

2. The method of claim 1, further comprising the step of engaging the outer cannula with the inner cannula, after the surgical workspace has been created, by rotating the inner cannula to turn a post on the inner cannula into a J-hook slot in the outer cannula.

3. The method of claim 1, wherein the joint surface comprises the articular surface of a knee.

4. The method of claim 1, wherein the soft tissue is engaged by rotating the threaded surface of the outer cannula into the soft tissue.

5. The method of claim 3, further comprising the step of inserting an osteochondral core through the inner cannula.

6. The method of claim 1, further comprising coupling the outer cannula to the inner cannula to maintain the surgical workspace.

7. The method of claim 1, further comprising:
   inserting at least one dilator into the incision made through the soft tissue;
   inserting the outer cannula over the at least one dilator before inserting the outer cannula into the incision; and
   removing the at least one dilator from the outer cannula before inserting the inner cannula into the outer cannula.

8. The method of claim 7, further comprising the step of slidably inserting a second dilator over the at least one dilator.

* * * * *